US00PP36267P3

(12) United States Plant Patent
Schoone

(10) Patent No.: US PP36,267 P3
(45) Date of Patent: Nov. 26, 2024

(54) ***PHALAENOPSIS* PLANT NAMED 'Mint'**

(50) Latin Name: *Phalaenopsis hybrida*
Varietal Denomination: Mint

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/527,362

(22) Filed: Dec. 3, 2023

(65) Prior Publication Data

US 2024/0188468 P1 Jun. 6, 2024

Related U.S. Application Data

(60) Provisional application No. 63/430,035, filed on Dec. 4, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'Mint', characterized by its upright plant habit; moderately vigorous to vigorous growth habit; strong flowering stems; strong leaves; freely flowering habit with typically two inflorescences developing per plant, each inflorescence with numerous flowers; flowers with light yellow green-colored petals, sepals and labella; and good postproduction longevity.

2 Drawing Sheets

Figure 1:
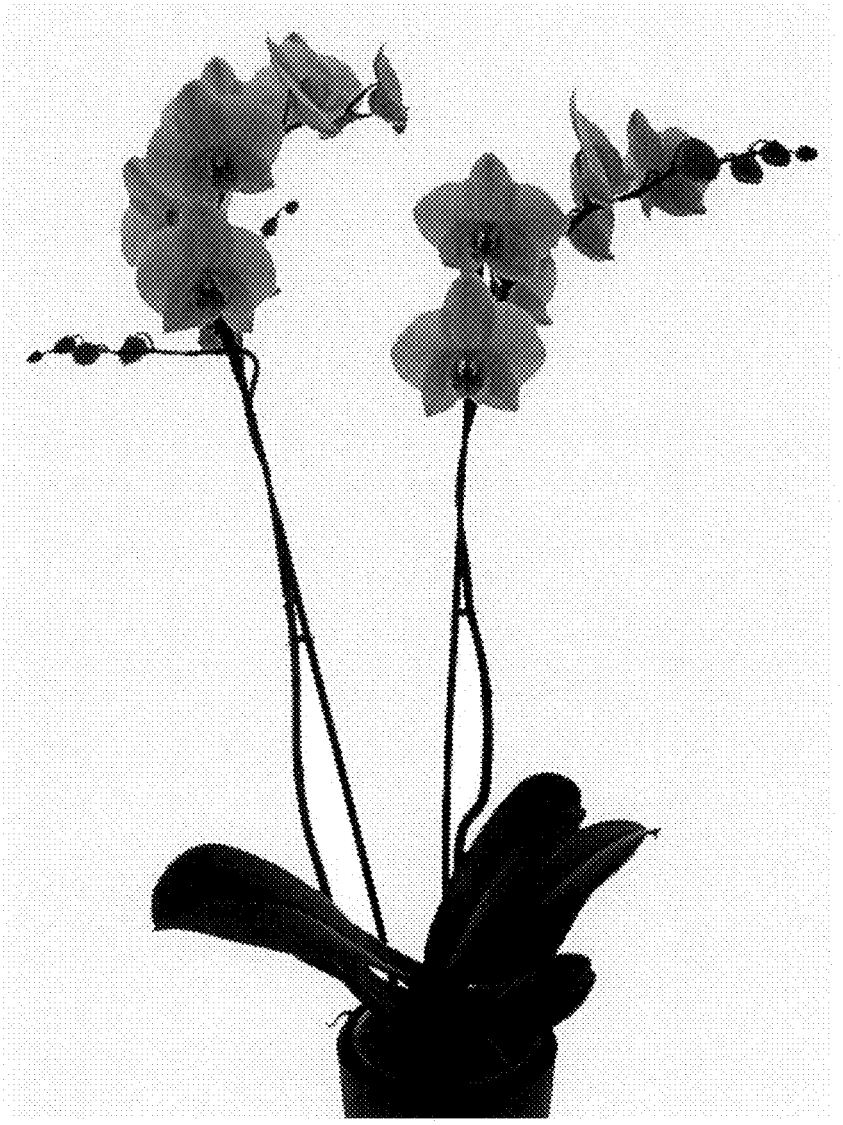

Botanical designation: *Phalaenopsis hybrida.*
Cultivar denomination: 'MINT'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Aug. 15, 2022, application number 2022/1915. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Mint'.

The new *Phalaenopsis* plant is a product of a planned breeding program conducted by the Inventor in Nantou, Taiwan; Heemskerk, The Netherlands; and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2012 in Nantou, Taiwan of a proprietary selection of *Phalaenopsis hybrida* identified as code number S3360, not patented, as the female, or seed, parent with *Phalaenopsis hybrida* 'Emeraude', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2018.

Asexual reproduction of the new *Phalaenopsis* plant by in vitro meristem propagation in a controlled environment in Assendelft, The Netherlands since October 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mint'. These characteristics in combination distinguish 'Mint' as a new and distinct *Phalaenopsis* plant:

1. Upright plant habit.
2. Moderately vigorous to vigorous growth habit.

3. Strong flowering stems.
4. Strong leaves.
5. Freely flowering habit with typically two inflorescences developing per plant, each inflorescence with numerous flowers.
6. Flowers with light yellow green-colored petals, sepals and labella.
7. Good postproduction longevity.

Plants of the new *Phalaenopsis* can be compared to plants of the female parent selection. Plants of the new *Phalaenopsis* differ primarily from plants of the female parent selection in flower column color as flower columns of plants of the new *Phalaenopsis* are yellow green in color whereas flower columns of plants of the female parent selection are white in color.

Plants of the new *Phalaenopsis* can be compared to plants of the male parent, 'Emeraude'. Plants of the new *Phalaenopsis* differ primarily from plants of 'Emeraude' in flower column color as flower columns of plants of the new *Phalaenopsis* are yellow green in color whereas flower columns of plants of 'Emeraude' are white in color. In addition, the labella lateral lobes of plants of the new *Phalaenopsis* are more curved than the labella lateral lobes of plants of 'Emeraude'.

Plants of the new *Phalaenopsis* can be compared to plants of *Phalaenopsis hybrida* 'Lemonade', not patented. In side-by-side comparisons, plants of the new *Phalaenopsis* differ primarily from plants of 'Lemonade' in the following characteristics:

1. Plants of the new *Phalaenopsis* are taller than plants of 'Lemonade'.
2. Leaves of plants of the new *Phalaenopsis* are not as elongated as leaves of plants of 'Lemonade'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Mint' grown in a container.

Figure 2:
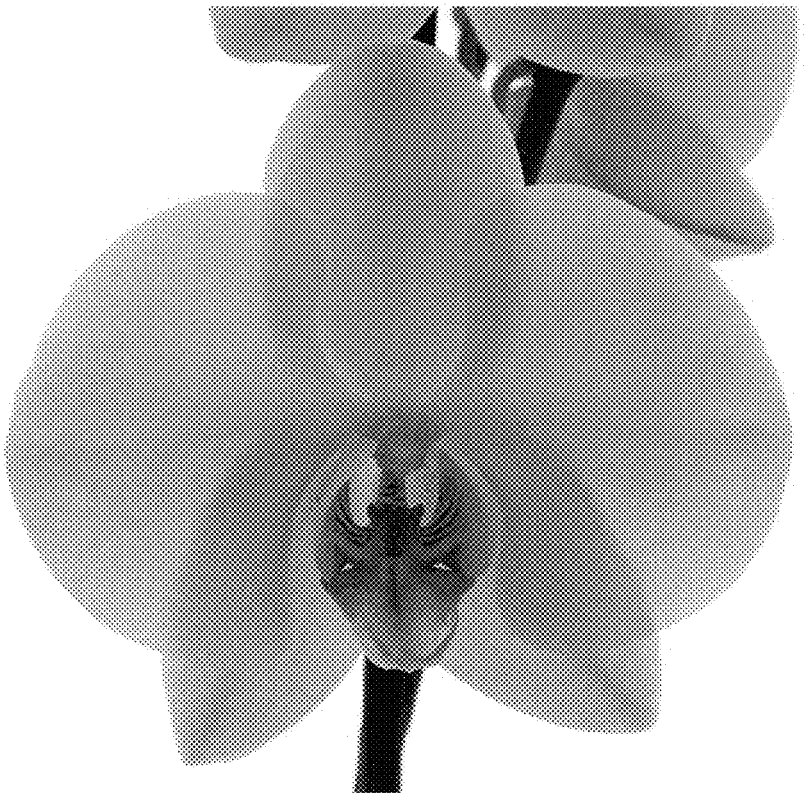

The photograph on the second sheet (FIG. 2) is a close-up view of a typical flower of 'Mint'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27 C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Mint'.

Parentage:

*Female, or seed, parent.*—Proprietary selection of *Phalaenopsis hybrida* identified as code number S3360, not patented.

*Male, or pollen, parent.*—*Phalaenopsis hybrida* 'Emeraude', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane.*—About 18 cm.

*Plant height, substrate level to top of floral plane.*—About 58.2 cm.

*Plant diameter or spread.*—About 35.9 cm.

Leaf description:

*Arrangement and quantity.*—Distichous, simple; sessile; about three fully-developed leaves per plant.

*Length.*—About 19.5 cm.

*Width.*—About 8.5 cm.

*Aspect.*—Semi-erect to horizontal and eventually outwardly arching.

*Shape.*—Narrowly elliptic to close to oblong; slightly carinate and apex, moderately reflexed.

*Apex.*—Unequal broadly acute to unequal obtuse.

*Base.*—Sheathing. Sheath length: About 2 cm. Sheath width: About 1.5 cm. Sheath color: Close to 143B; proximally, close to 143C.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to a blend of NN137A and 147A. Developing leaves, lower surface: Close to 146A; at the margins, tinged with close to N186C. Fully expanded leaves, upper surface: Close to NN137A; venation, close to 147A. Fully expanded leaves, lower surface: Close to 146B; venation, close to 143A.

Inflorescence description:

*Appearance and flowering habit.*—Showy zygomorphic flowers arranged on axillary simple or branched racemes; typically two inflorescences develop per plant; each inflorescence with about 14 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 30.5 cm.

*Inflorescence width*.—About 15 cm.

*Flower buds*.—Height: About 2.1 cm. Diameter: About 1.5 cm by 1.8 cm. Shape: Broadly ovate. Color: Close to N144D.

*Flower size*.—About 7.2 cm (vertical) by 8.5 cm (horizontal).

*Flower depth*.—About 2.8 cm.

*Petals, quantity and arrangement*.—Three, two lateral petals and one center petal transformed into a labellum.

*Lateral petals*.—Length: About 4 cm. Width: About 5 cm. Shape: Close to lunate. Apex: Broadly obtuse. Margin: Entire; not undulate. Texture and luster, upper and lower surfaces: Smooth, glabrous, velvety; matte. Color: When opening, upper surface: Close to 149D. When opening, lower surface: Close to 145C; towards the margins and apex, close to 149D. Fully opened, upper surface: Close to a blend of 145D and 150D; color does not change with subsequent development. Fully opened, lower surface: Close to 145C; towards the margins and apex, close to 145D; color does not change with subsequent development.

*Labella*.—Appearance: Three-parted with two lateral lobes and a central lobe. Length, lateral lobes: About 2.1 cm. Width, lateral lobes: About 1.7 cm. Length, central lobe: About 2 cm. Width, central lobe: About 5.5 mm to 20 mm. Length, cirrhose tips: About 1.5 cm. Shape, lateral lobes: Broadly elliptic to close to rhomboid. Shape, central lobe: Deltoid. Apex, lateral lobes: Obtuse. Apex, central lobe: Cleft with two reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 5 mm in height. Color: When opening, upper surface: Lateral lobes: Close to a blend of 145D and 149D; towards the base, close to 150C with stripes, close to 184A. Central lobe: Close to 149D; towards the base, close to 177C and 177D and at the base, close to 145C with stripes, close to 178B; midvein, close to 177C and 177D; cirrhose tips, close to 145B. Callosities: Close to 7B; fine dots, close to 177A. When opening, lower surface: Lateral lobes: Close to 145C; proximal margins, tinged with close to 150B and edges, close to 175C. Central lobe: Close to 149D; proximal margins, close to 174A; at the base, close to 145B; cirrhose tips, close to 145B. Fully opened, upper surface: Lateral lobes: Close to a blend of 145D and 149D; towards the base, close to 150C with stripes, close to 178A. Central lobe: Close to a blend of 149D and 150D; towards the base, close to 177C and 177D and at the base, close to 145C with stripes, close to 178B; midvein, close to 177C and 177D; cirrhose tips, close to 151D. Callosities: Close to 13A; fine dots, close to 175A. Fully opened, lower surface: Lateral lobes: Close to 145C; proximal margins, tinged with close to 154C and edges, close to 175C. Central lobe: Close to 145C; towards the margins, close to 145D; proximal margins, close to 174A; at the base, close to 145B; cirrhose tips, close to 151D.

*Sepals*.—Quantity and arrangement: Three, one upper dorsal sepal and two lower lateral sepals. Length, dorsal sepal: About 4.2 cm. Width, dorsal sepal: About 3.2 cm. Length, lateral sepals: About 4.3 cm. Width, lateral sepals: About 2.7 cm. Shape, dorsal sepal: Broadly elliptic. Shape, lateral sepals: Ovate. Apex, dorsal sepal: Minutely retuse. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 145C. When opening, lower surface: Close to 145B; towards the apex, close to 145A; at the margins, close to 145C. Fully opened, upper surface: Close to a blend of 145D and 149D; color does not change with subsequent development. Fully opened, lower surface: Close to 145C; towards the apex, tinged with close to 152D; at the margins, close to 145D; color does not change with subsequent development. Color, lateral sepals: When opening, upper surface: Close to 145C; towards the base, close to 145B with fine dots, close to 177A and 177B. When opening, lower surface: Close to 145B. Fully opened, upper surface: Close to a blend of 145D and 149D; towards the base, close to 145C with fine dots, close to 182B and 182C; color does not change with subsequent development. Fully opened, lower surface: Close to 145C; towards the margins, close to 145D; midvein, close to 144D; color does not change with subsequent development.

*Peduncles*.—Length: About 63.2 cm. Diameter: About 6.5 mm. Strength: Strong. Aspect: Upright to outwardly arching. Texture and luster: Smooth, glabrous; matte. Color: Close to 147A with fine dots and marbling, close to 148D.

*Pedicels*.—Length: About 4.2 cm. Diameter: About 3 mm. Strength: Moderately strong. Aspect: About 50 degrees From peduncle axis. Texture and luster: Smooth, glabrous; matte. Color: Close to 145A; proximally, close to 144A and 144B and distally, close to 144B.

*Reproductive organs*.—Androecium: Column length: About 8 mm. Column width: About 5.5 mm. Column color: Close to 145B. Pollinia quantity: Two. Pollinia diameter (per two pollinia): About 2.5 mm. Pollinia color: Close to 24A. Gynoecium: Stigma length: About 4 mm. Stigma width: About 3 mm. Stigma shape: Reniform. Stigma color: Close to 147D. Ovary length: About 1.1 cm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Mint' as illustrated and described.

* * * * *